(12) United States Patent
Morelle et al.

(10) Patent No.: US 7,271,129 B1
(45) Date of Patent: Sep. 18, 2007

(54) COMPOSITIONS FOR IMPROVING CROP PRODUCTION, THE QUALITY AND PROTECTION THEREOF

(76) Inventors: Jean Morelle, 170, Avenue Parmentier, 75010 Paris (FR); Eliane Lauzanne, 57, Avenue De La Republique, 75011 Paris (FR); Christophe De Mil, 7, Rue Mechain, 75014 Paris (FR)

( * ) Notice: Subject to any disclaimer, the term of this patent is extended or adjusted under 35 U.S.C. 154(b) by 0 days.

(21) Appl. No.: 09/463,536

(22) PCT Filed: Feb. 11, 1999

(86) PCT No.: PCT/FR99/00297

§ 371 (c)(1),
(2), (4) Date: Aug. 18, 2000

(87) PCT Pub. No.: WO99/48364

PCT Pub. Date: Sep. 30, 1999

(30) Foreign Application Priority Data

Mar. 26, 1998 (FR) .................................. 98 03723

(51) Int. Cl.
*A01N 59/00* (2006.01)
*A01N 37/00* (2006.01)
(52) U.S. Cl. ........................ 504/187; 504/307; 504/320
(58) Field of Classification Search ................ 504/600, 504/187
See application file for complete search history.

(56) References Cited

U.S. PATENT DOCUMENTS 4,797,151 A * 1/1989 DeMil ......................... 71/113

FOREIGN PATENT DOCUMENTS

GB 2097256 * 11/1982

* cited by examiner

*Primary Examiner*—Alton Pryor
(74) *Attorney, Agent, or Firm*—Lucas & Mercanti, LLP

(57) ABSTRACT

This invention concerns the creation of compounds destined for agricultural use, characterized by butyric amino acids and caprylic amino acids, either salified or not with zinc and copper salts, which, administered in small doses per hectare, have been proven to lead to an increase in crop yield and quality.

3 Claims, No Drawings

COMPOSITIONS FOR IMPROVING CROP PRODUCTION, THE QUALITY AND PROTECTION THEREOF

French Patent Number 77 27703 is intended to protect the use of a certain number of lipo-amino acid structures/compounds for agricultural purposes, research having demonstrated their general activity on chlorophyllous function. There were no teachings provided concerning the nature of the compounds used, the nature of the plants or the conditions which would maximize crop yields. Consequently, it has been noted that several other variables which can impact results positively or negatively need to be taken into consideration.

In effect, twenty years of research has led to the discovery that the compounds indicated in this patent do not, in and of themselves, guarantee favorable results without taking into account numerous other parameters: the nature of the molecule, concentrations of the molecules per hectare, the moment of application based upon the life cycle of the plant in question, its nature, the state of the soil and climactic conditions.

Thus, in light of several experiments performed in the field we have reached the surprising conclusion that certain lipo-amino acid elements as opposed to others, salified or not by oligoelements such as copper and zinc, had an efficacy comparable to plant hormones (auxins) given the low quantity needed per hectare: a dose of 6 g./hectare, in an anhydrous compound, is sufficient for obtaining positive results in certain crop types.

These observations show us that the application of the compounds indicated in various patents will require further study in order to obtain the desired results.

It has been ascertained that the activity was linked to the hydrosolubility of the compound, which is found in the butyric chain and the caprylic chain but not in the other fatty acid chains.

It has been surprising to observe that the zinc salts of the butyric-amino acids also protected crops by repelling animals destructive to them, such as birds, rabbits, wild boar, etc.

Additionally, this structure increases the germinal capacities as well as root development, contrary to copper salts or the zinc salts of caprylic-amino acids.

Only a few grams of zinc salts (between 5 and 10 grams) of butyric-amino acids for 100 to 150 kilograms of crops are required in order to obtain the specified activity.

Only 0.036 to 0.36 mol. of copper salts of caprylic-amino acids are necessary to increase the sugar content of beets and grapes by 5 to 10%. Beyond the ordinary doses, one exceeds optimal efficacy without any detrimental effects to the plant.

Only 0.1 mol of copper salts of butyric-amino acids are necessary in order to obtain a 5 to 10% increase in crop yields of legumes (peas, green beans).

In the case of potato cultivation, if one treats the crop with two times 50 g. of copper salts of butyric-amino acids (0.2 mol/hectare) at the end of the tuberisation phase, one obtains an increase in crop yield of 4 metric tons per hectare. These results are a measurable improvement over those obtained with copper salts of caprylic-amino acids.

Other benefits observed are more uniform tubers, of a higher caliber and a general increase in the quality of crop yield. However, if the treatment is applied during the tuberisation phase, the development cycle will be disturbed and the results alluded to earlier will not be obtained.

As far as cereals are concerned, it has been determined that it is preferable to use the caprylic chain salified by copper, treating either during ear emergence or during flowering, specifically several treatments in the dosage of 6 g./hectare (0.01 mol) or one treatment of 60 g. (0.1 mol).

Finally, it has been concluded that the zinc and copper salts of the butyric-amino acids proved detrimental to the flower and it is therefore imperative to use the product in a non-salified form in a dose of 60-100 g./hectare.

Thus, in the case of this patent, we have determined that it is preferable to use chains of fatty acids with four to eight atoms of carbon, specifically the butyric chain and the caprylic chain, acylated to the amino acids derived from hydrolysates of animal proteins, including those derived from fish, as well as vegetable-based ones.

It has also been observed that the final activity of the acylates was dependent upon the nature of the fatty acid chain and the nature of the oligoelement; however, it was not influenced, except in some particular situations, by the nature of the hydrolyzed amino acids.

This invention concerns the increase of crop yields of agricultural products, notably those of specifically biological origin since the treatment is of organic origin and non-polluting because of the low concentration required (less than one molecule per hectare) of butyric and caprylic lipo-amino acids and their copper and zinc salts.

The invention extends equally to the protection of crops or leaves against viruses (such as tobacco mosaic), microorganisms (with the use of copper salts of the caprylic amino acids, as well as the protection of the crops in question against potentially destructive animals through the use of zinc salts of the butyric-amino acids) in which case only 3 to 5 g. of active product is required for the protection of 100-150 kg. of crops.

The invention claimed is:

1. A method for increasing the sugar content of beets, said method comprising administration of copper salts of caprylic amino acids to beet crops in an amount effective to increase the sugar content of said beets.

2. A method of treating potatoes to increase crop yield by administering to a potato crop, at the end of the tuberisation phase, two doses of 50 g. each per hectare of copper salts of butyric-amino acids.

3. A method of treating potatoes to increase crop yield by administering to a potato crop, at the end of the tuberisation phase, copper salts of butyric-amino acids in an amount effective to increase the crop yield of said potato crop.

* * * * *